(12) United States Patent
Ma

(10) Patent No.: US 12,336,926 B2
(45) Date of Patent: Jun. 24, 2025

(54) EXTERNAL NASAL DILATION DEVICE

(71) Applicant: Junkun Ma, Hoover, AL (US)

(72) Inventor: Junkun Ma, Hoover, AL (US)

(*) Notice: Subject to any disclaimer, the term of this patent is extended or adjusted under 35 U.S.C. 154(b) by 340 days.

(21) Appl. No.: 18/116,808

(22) Filed: Mar. 2, 2023

(65) Prior Publication Data

US 2023/0277357 A1 Sep. 7, 2023

Related U.S. Application Data

(60) Provisional application No. 63/317,202, filed on Mar. 7, 2022.

(51) Int. Cl.
*A61F 5/08* (2006.01)

(52) U.S. Cl.
CPC ..................... *A61F 5/08* (2013.01)

(58) Field of Classification Search
CPC .... A61F 5/08; A61F 13/26; A61M 2210/0618
See application file for complete search history.

(56) References Cited

U.S. PATENT DOCUMENTS

| | | | |
|---|---|---|---|
| 5,850,834 A | 12/1998 | Yoshida | |
| 9,775,738 B2 | 10/2017 | Andre | |
| 9,901,480 B2 | 2/2018 | Ierulli | |
| 10,556,095 B2 | 2/2020 | Castillo | |
| 10,675,174 B2 | 6/2020 | Castillo | |
| 2012/0209313 A1 | 8/2012 | Ierulli | |
| 2015/0250637 A1* | 9/2015 | Ierulli | A61F 5/08 606/204.45 |

FOREIGN PATENT DOCUMENTS

| | | |
|---|---|---|
| JP | H10286313 | 4/1997 |
| WO | WO2019114982 | 5/2017 |

\* cited by examiner

*Primary Examiner* — Majid Jamialahmadi

(57) ABSTRACT

An external nasal dilation device for enhancing nasal airflow includes a pair of pads, each of which has adhesive positioned on its lower face. The adhesive is used to removably attach the pads to opposed sides of a nose of a user. Each flap of a pair of flaps is hingedly attached to an upper face of a respective pad so that the flap is hingable relative to the respective pad. A panel is attached to and extends between the flaps. The panel is resiliently flexible so that the panel extends arcuately over a bridge of the nose. The panel exerts opposing forces to nostrils of the user to expand the nostrils, thereby enhancing nasal airflow through the nostrils.

14 Claims, 8 Drawing Sheets

EXTERNAL NASAL DILATION DEVICE

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to nasal dilators and more particularly pertains to a new nasal dilator for enhancing nasal airflow. The present invention discloses a nasal dilator wherein a resiliently flexible panel bridges the nasal passages without contacting the nose, thereby effecting nasal dilation without the discomfort of prior art nasal dilator.

(2) Description of Related Art Including Information Disclosed Under 37 CFR 1.97 and 1.98

The prior art relates to nasal dilators, which may comprise elongate strips having adhesive positioned adjacent their opposed ends, nasal dilators utilizing magnetic connections, and nasal dilators with flaps that are not used for connective purposes. What is lacking in the prior art is a nasal dilator comprising a pair of pads, which are adhesively attachable to opposed sides of a user's nose and each of which has a flap hingedly attached. A resiliently flexible panel, which is attached to and which extends between the flaps, exerts opposing forces to the nostrils but does not contact, nor is it adhered to, the nose.

BRIEF SUMMARY OF THE INVENTION

An embodiment of the disclosure meets the needs presented above by generally comprising a pair of pads, each of which has adhesive positioned on its lower face. The adhesive is configured to removably attach the pads to opposed sides of a nose of a user. Each flap of a pair of flaps is hingedly attached to an upper face of a respective pad so that the flap is hingable relative to the respective pad. A panel is attached to and extends between the flaps. The panel is resiliently flexible so that the panel extends arcuately over a bridge of the nose. The panel is configured to exert opposing forces to nostrils of the user to expand the nostrils, thereby enhancing nasal airflow through the nostrils.

Another embodiment of the disclosure includes a method of dilating nostrils of a user, which comprises a provision step that entails providing an external nasal dilation device, according to the disclosure above. Use steps of the method are removably attaching one pad to one opposed side of a nose of the user, using the adhesive, flexing the panel to position the other pad proximate to the other opposed side of the nose, removably attaching the other pad to the other opposed side of the nose using the adhesive, and allowing the panel to exert opposing forces to the nostrils of the user to expand the nostrils.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(J) DETAILED DESCRIPTION OF THE INVENTION

Figure 1:
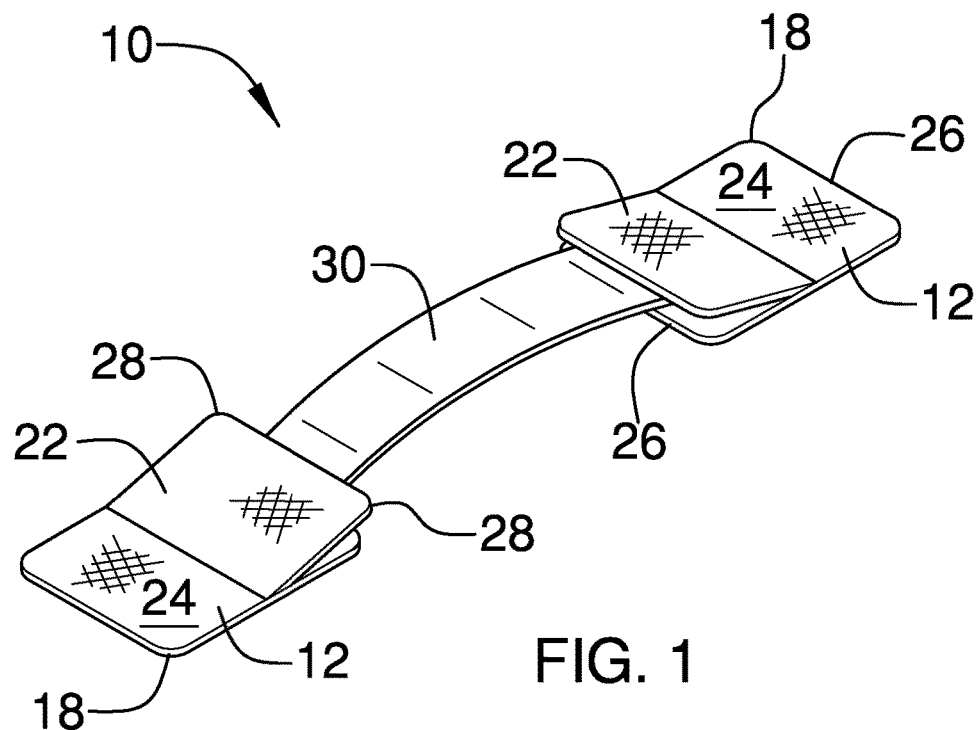
FIG. 1 is a top isometric perspective view of an external nasal dilation device according to an embodiment of the disclosure.

With reference now to the drawings, and in particular to FIGS. 1 through 13 thereof, a new nasal dilator embodying the principles and concepts of an embodiment of the disclosure and generally designated by the reference numeral 10 will be described.

As best illustrated in FIGS. 1 through 13, the external nasal dilation device 10 generally comprises a pair of pads 12, each of which has adhesive 14 positioned on its lower face 16. The adhesive 14 is configured to removably attach the pads 12 to opposed sides of a nose of a user, as shown in FIG. 12. The pads 12 may be substantially rectangular and corners 18 of the pads 12 may be arcuate, as shown in FIG. 1. The present invention also anticipates the pads 12 being square, oval, circular, or irregularly shaped and the corners 18 being right angled, or the like, as shaping of the pads 12 and the corners 18 is not critical to functioning of the nasal dilation device 10. The present invention anticipates the pads 12 being one or both of porous and perforated so as to be breathable, thereby reducing risk of irritation to underlying skin and allowing the underlying skin to breath.

Figure 2:
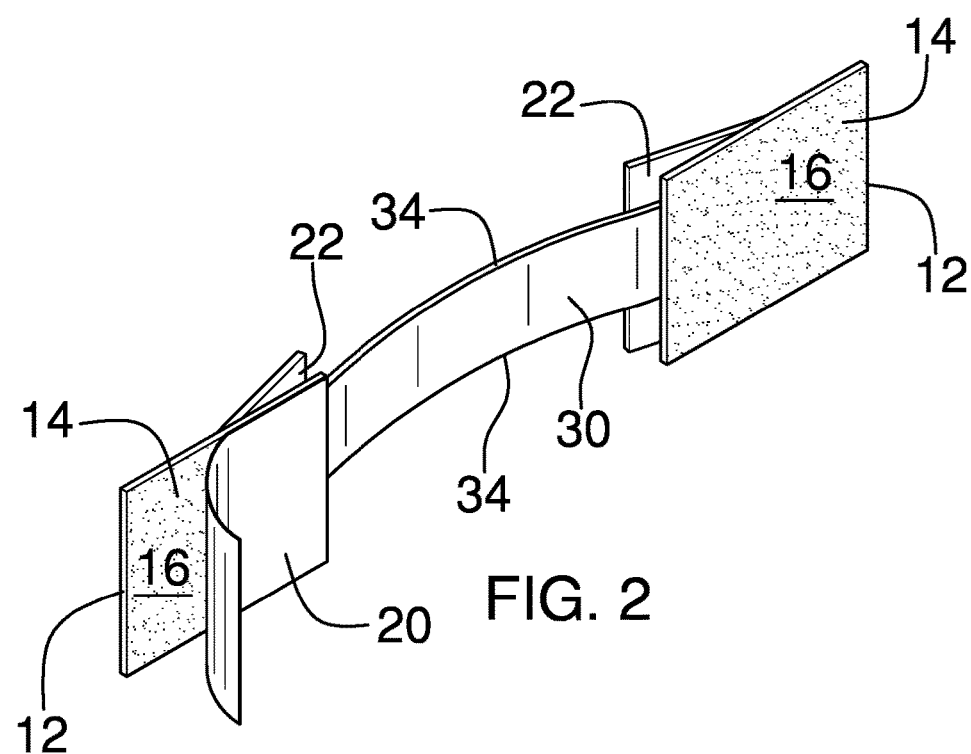
FIG. 2 is a bottom isometric perspective view of an embodiment of the disclosure.
Figure 8:
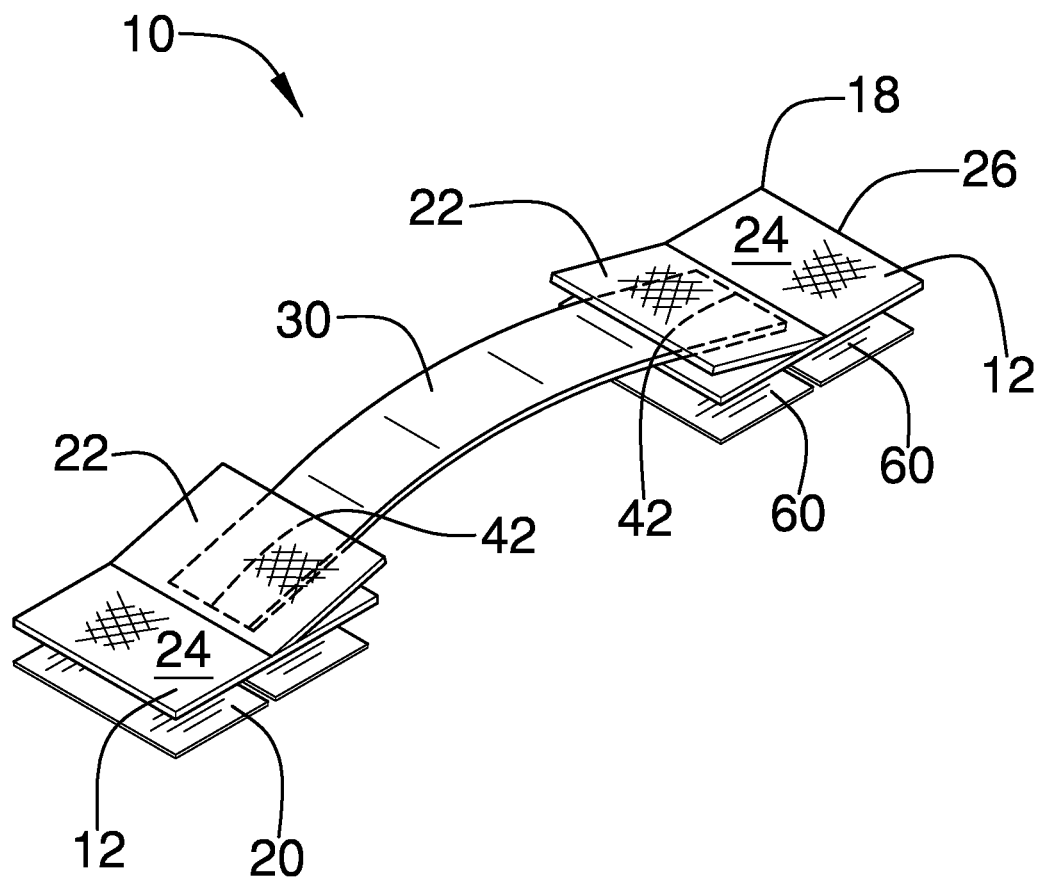
FIG. 8 is a top isometric perspective view of an embodiment of the disclosure.

The external nasal dilation device 10 also may comprise a pair of sheets 20. Each sheet 20 is removably attached to the adhesive 14 positioned on a respective pad 12 so that the adhesive 14 is substantially covered by the sheet 20, as shown in FIG. 2. The sheet 20 is selectively detachable from the respective pad 12 to expose the adhesive 14. The sheets 20 are configured to prevent inadvertent adhesion of the adhesive 14. As is shown in FIG. 8, each sheet 20 may comprise a pair of sections 60, thereby allowing the user to sequentially expose the adhesive 14.

Figure 3:
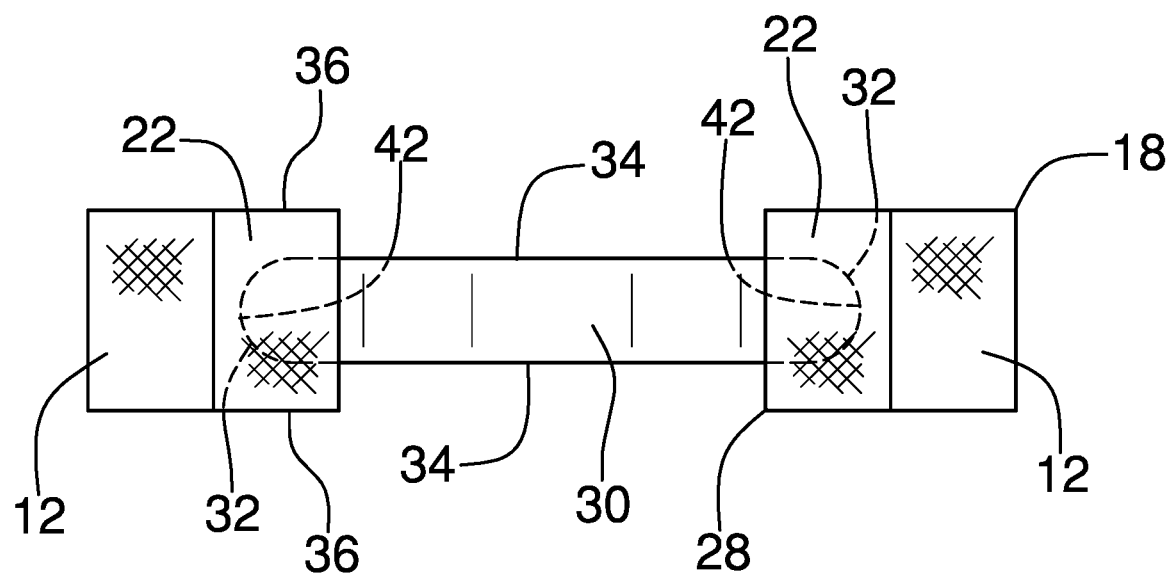
FIG. 3 is a bottom view of an embodiment of the disclosure.

Each flap 22 of a pair of flaps 22 is hingedly attached to an upper face 24 of a respective pad 12 so that the flap 22 is hingable relative to the respective pad 12. As shown in FIG. 3, the flap 22 is attached to the respective pad 12 substantially equally distant from opposed ends 26 of the respective pad 12. As will become apparent, the flap 22 being positioned substantially equally distant from opposed ends 26 of the respective pad 12 serves to distribute shear force applied to the respective pad 12 through the flap 22. The flaps 22 may be substantially rectangular and corners 28 of the flaps 22 that are distal from the pads 12 may be arcuate, as shown in FIG. 1. The present invention also anticipates the flaps 22 being square, trapezoidal, or the like, and the corners 28 being right angled, as shown in FIG. 2, or the like, as shaping of the flaps 22 and the corners 28 is not critical to functioning of the nasal dilation device 10.

Figure 5:
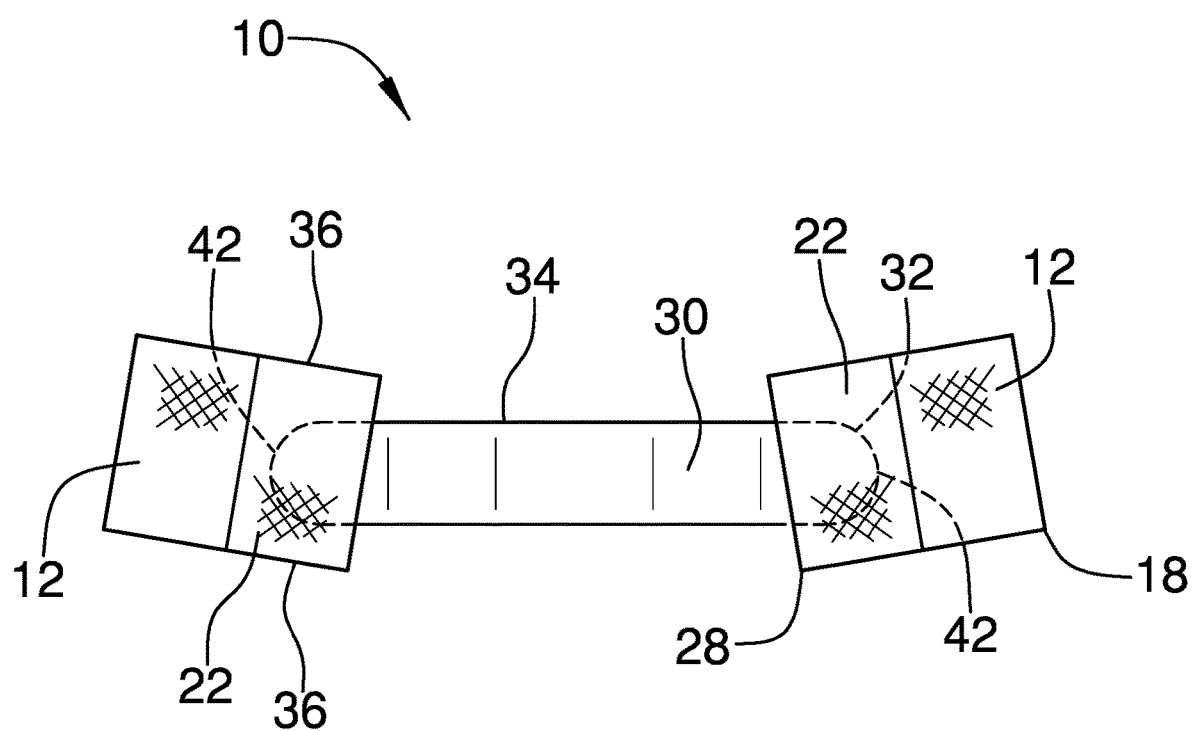
FIG. 5 is bottom view of an embodiment of the disclosure.

A panel 30 is attached to and extends between the flaps 22. The panel 30 is substantially rectangular, as shown in FIGS. 3 and 5, square, trapezoidal, or the like, and corners 32 of the panel 30 may be arcuate, as shown in FIGS. 3 and 5, right angled, or the like. The panel 30 is resiliently flexible so that the panel 30 extends arcuately over a bridge of the nose. As shown in FIG. 3, the panel 30 may be dimensionally narrower than the flaps 22, thus reducing potential of the panel 30 contacting the bridge of the nose. The present invention also anticipates the panel 30 being of substantially equivalent width to the flaps 22 and wider than the flaps 22.

Figure 4:
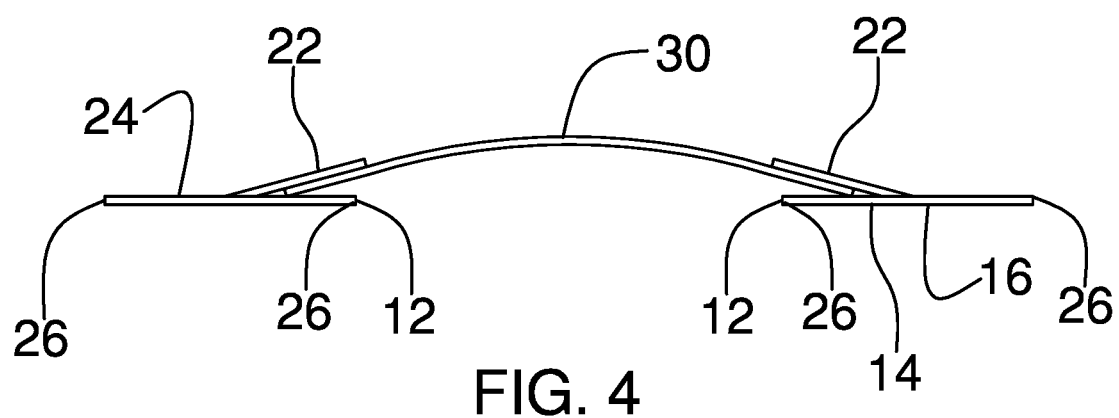
FIG. 4 is a side view of an embodiment of the disclosure.

The panel 30 comprises one or more of spring metal, plastic, or elastomer and is configured to exert opposing forces to nostrils of the user to expand the nostrils, thereby enhancing nasal airflow through the nostrils. The panel 30, being resiliently flexible, may have a default configuration that is arcuate, as shown in FIGS. 1, 2, and 4, or may have a default configuration that is planar. Flexing of the panel 30 positions it a tensioned configuration, as shown in FIG. 12, wherein the opposing forces are applied to the nostrils. Of note, the panel 30 does not contact skin of the nose, thereby eliminating potential irritation to the skin and allowing the skin to breath. Advantageously, relative to prior art nasal dilators, the panel 30 of the external nasal dilation device 10 reduces peel forces applied to the pads 12, thereby stabilizing the external nasal dilation device 10 in position on the nose.

As shown in FIG. 3, opposed side edges 34 of the panel 30 are substantially parallel to opposing edges 36 of the flaps 22. The opposed side edges 34 of the panel 30 also may be non-parallel to the opposing edges 36 of the flaps 22, as shown in FIG. 5. The different configurations of the external nasal dilation device 10 shown in FIGS. 3 and 5 allow the external nasal dilation device 10 to accommodate variation of structure of noses of users.

Figure 6:
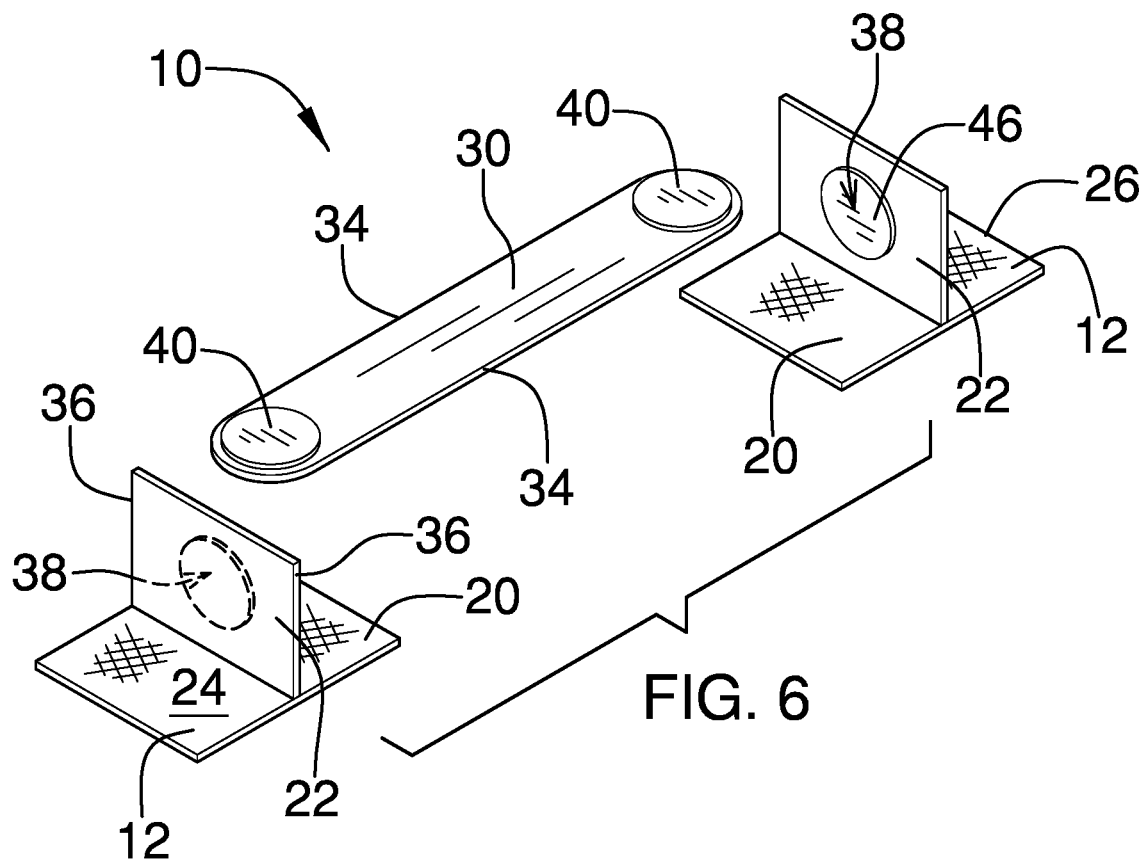
FIG. 6 is an exploded view of an embodiment of the disclosure.
Figure 7:
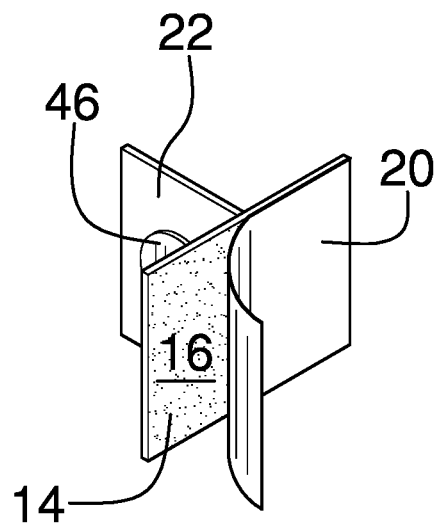
FIG. 7 is a detail view of an embodiment of the disclosure.

As shown in FIGS. 6 and 7, the external nasal dilation device 10 also may comprise a pair of first connectors 38 and a pair of second connectors 40. Each first connector 38 is attached to a respective flap 22 and each second connector 40 is attached to the panel 30 proximate to a respective opposing end 42 of the panel 30. The second connectors 40 are complementary to the first connectors 38 so that each second connector is positioned to selectively engage a respective first connector 38 to removably attach the panel 30 to the pair of flaps 22.

At least one of the second connector 40 and the respective first connector 38 comprises a magnet 44. For example, the second connector 40 may comprise a magnet 44 and the respective first connector 38 may comprise a ferromagnetic disc 46, or vice versa. The present invention also anticipates each of the second connector 40 and the respective first connector 38 comprising a magnet 44, with the magnets 44 having complementary polarity. Additionally, the present invention anticipates other connecting means for removably attaching the panel 30 to the pair of flaps 22, such as, but not limited to, hook and loop fasteners, clips, or the like.

Figure 9:
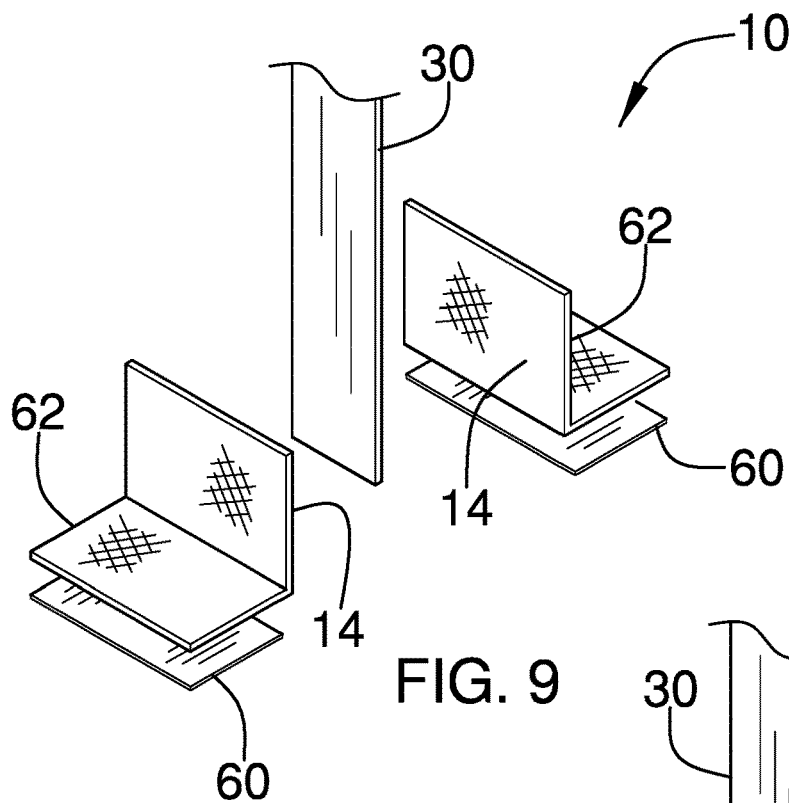
FIG. 9 is an exploded view of an embodiment of the disclosure.
Figure 10:
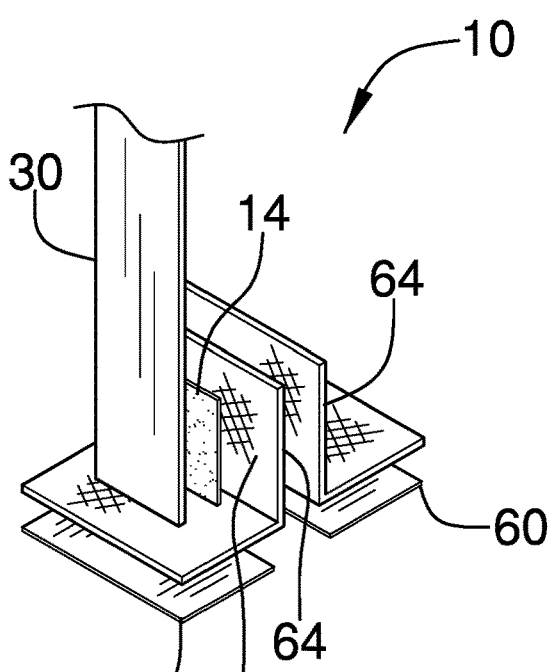
FIG. 10 is an exploded view of an embodiment of the disclosure.
Figure 11:
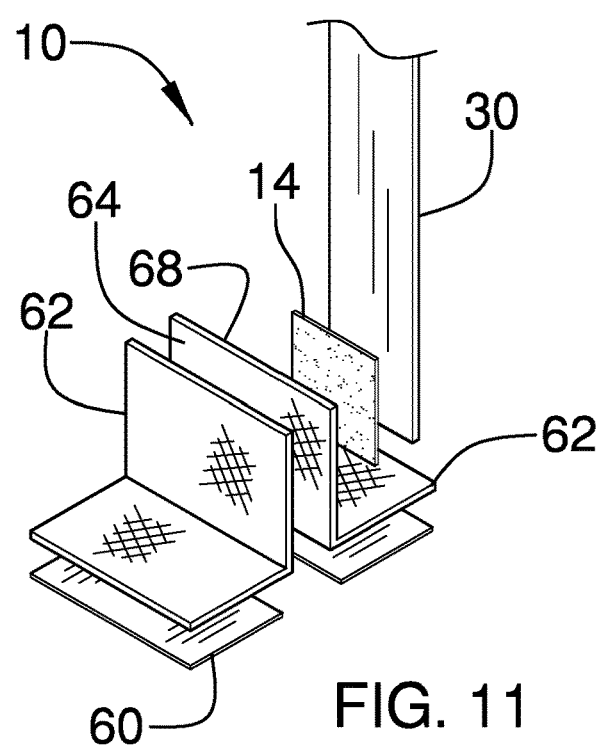
FIG. 11 is an exploded view of an embodiment of the disclosure.
Figure 12:
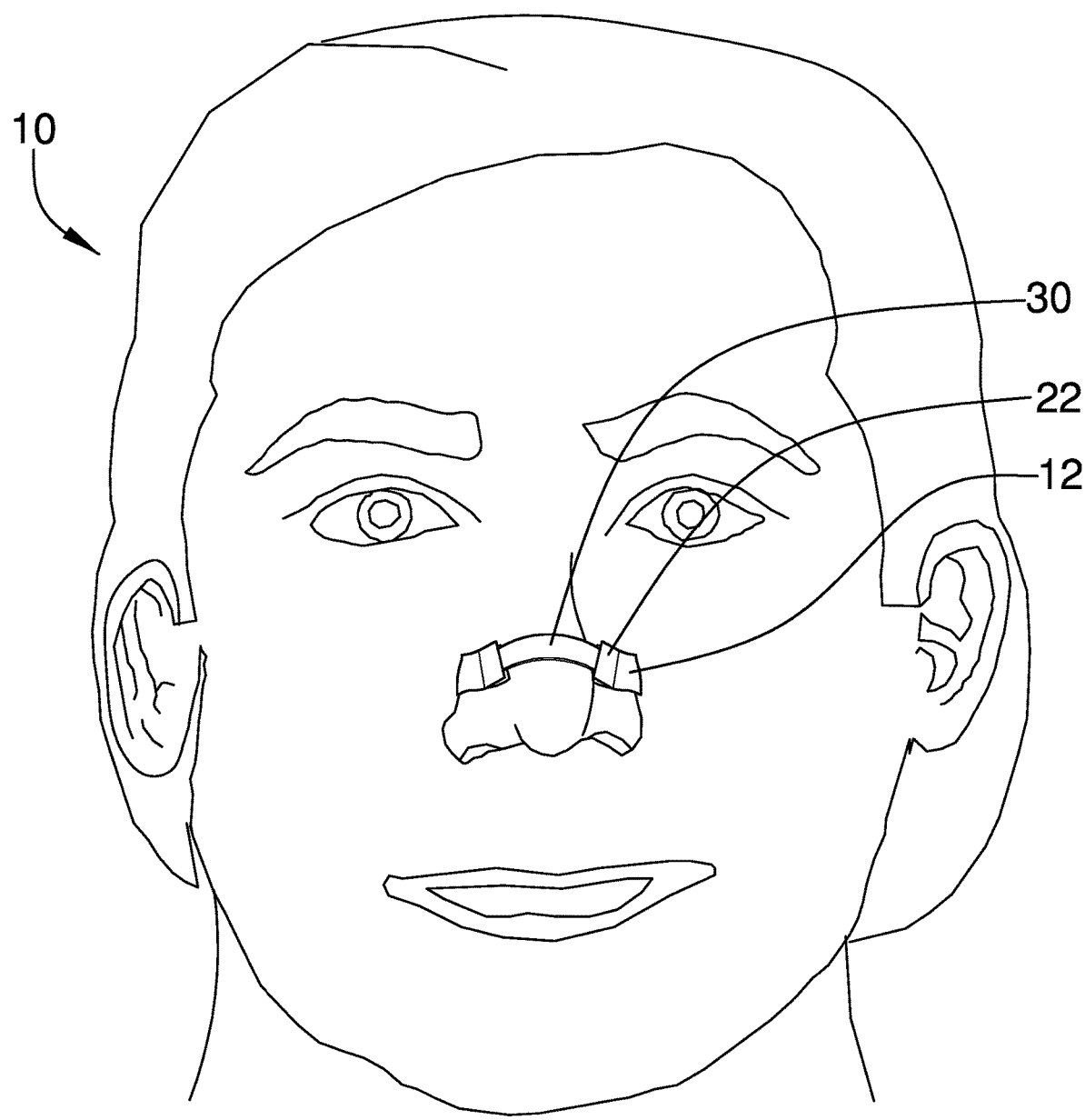
FIG. 12 is an in-use of an embodiment of the disclosure.
Figure 13:
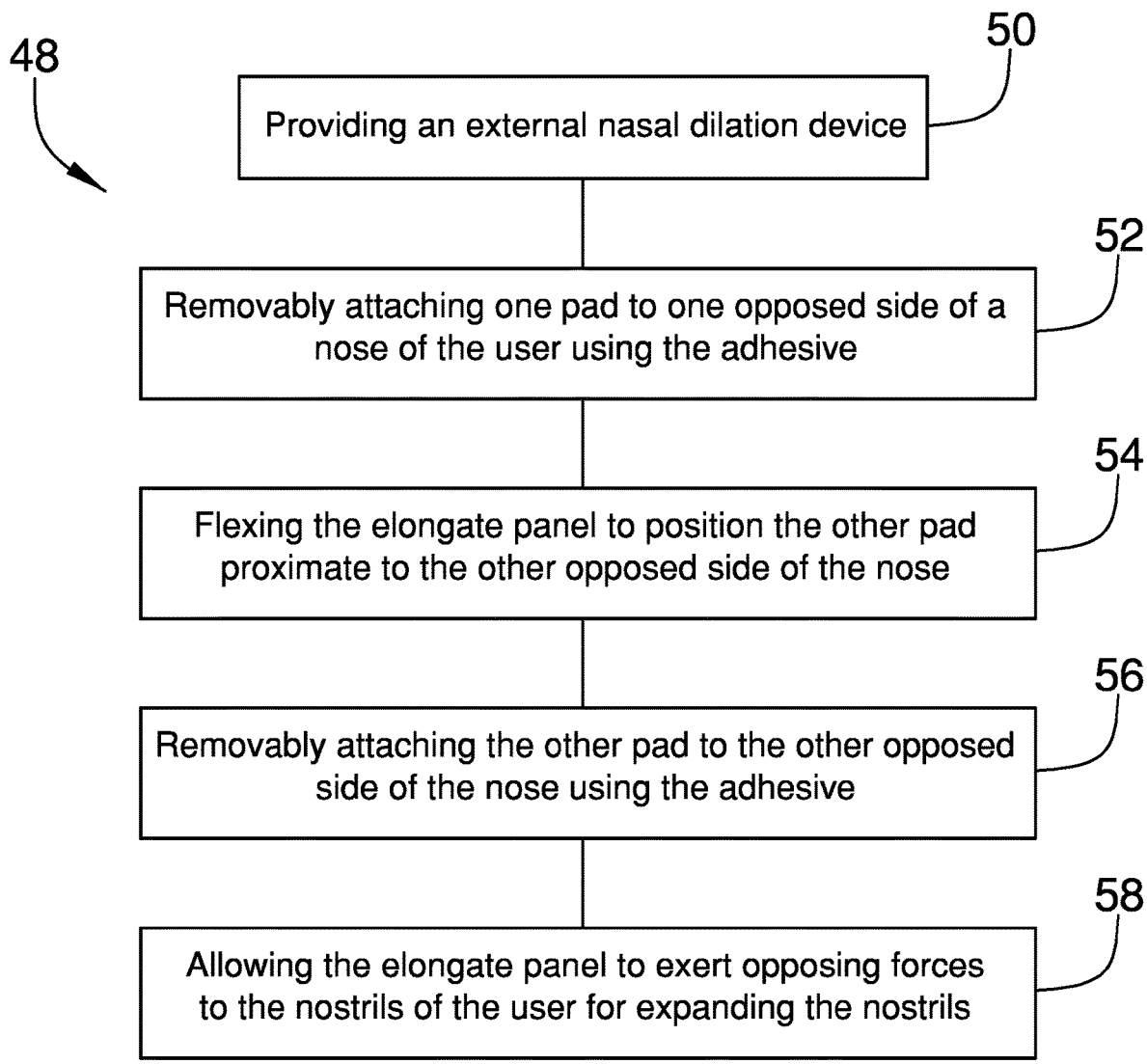
FIG. 13 is a flow diagram for a method utilizing an embodiment of the disclosure.

FIGS. 9-11 depict alternative, nonlimiting, configurations of the external nasal dilation device 10 that are anticipated by the present invention. Conceptually, each pad 12 and its attached flap 22 has been bisected to generate a pair of attachment pieces 62. As shown in FIG. 9, adhesive 14 may be positioned on each flap section 64 of the attachment pieces 62, allowing the panel 30 to be attached between the flap sections 64. Alternatively, adhesive 14 may be attached to an outer face 66 of each of the flap sections 64, as shown in FIG. 10, so that the panel 30 pulls the flaps 22 outwardly from the nostrils. Another alternative configuration, shown in FIG. 11, has the adhesive 14 disposed on an inner face 68 of each of the flap sections 64 so that the panel 30 pushes the flaps 22 outwardly from the nostrils. For each configuration shown in FIGS. 9-11, the present invention also anticipates the adhesive 14 being positioned on the panel 30.

In use, the external nasal dilation device 10 enables a method of dilating nostrils of a user 48, which is shown in FIG. 9. The method 48 comprises a provision step 50, which entails providing an external nasal dilation device 10, according to the specification above. A first use step 52 of the method 48 is removably attaching one pad 12 to one opposed side of a nose of the user using the adhesive 14. A second use step 54 of the method 48 is flexing the panel 30 to position the other pad 12 proximate to the other opposed side of the nose, with the panel 30 extending arcuately over a bridge of the nose. A third use step 56 of the method 48 is removably attaching the other pad 12 to the other opposed side of the nose using the adhesive 14. A fourth use step 58 of the method 48 is allowing the panel 30 to exert opposing forces to the nostrils of the user to expand the nostrils.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An external nasal dilation device comprising:
    a pair of pads;
    adhesive positioned on a lower face of each pad of the pair of pads, wherein the adhesive is configured for removably attaching the pads of the pair of pads to opposed sides of a nose of a user;
    a pair of flaps, each flap of the pair of flaps being hingedly attached to an upper face of a respective pad of the pair of pads, such that each flap of the pair of flaps is hingable relative to the respective pad;
    a panel attached to and extending between the flaps of the pair of flaps, the panel being resiliently flexible, such that the panel is configured to extends arcuately over a bridge of the nose, wherein the panel is configured for exerting opposing forces to nostrils of the user for expanding the nostrils;
    a pair of first connectors, each first connector of the pair of first connectors being attached to a respective flap of the pair of flaps; and
    a pair of second connectors, each second connector of the pair of second connectors being attached to the panel proximate to a respective opposing end of the panel, the second connectors being complementary to the first connectors, such that each second connector of the pair of second connectors is positioned for selectively engaging a respective first connector of the pair of first connectors for removably attaching the panel to the pair of flaps.

2. The external nasal dilation device of claim 1, further including a pair of sheets, each sheet of the pair of sheets being removably attached to the adhesive positioned on a respective pad of the pair of pads, such that the adhesive is substantially covered by the sheet, the sheet being selectively detachable from the respective pad for exposing the adhesive, wherein the sheets are configured for preventing inadvertent adhesion of the adhesive.

3. The external nasal dilation device of claim 1, wherein each flap of the pair of flaps is attached to the respective pad substantially equally distant from opposed ends of the respective pad.

4. The external nasal dilation device of claim 1, wherein the panel comprises one or more of elastomer, plastic, and spring metal.

5. The external nasal dilation device of claim 1, wherein:
    the pads of the pair of pads are substantially rectangular, square, oval, or circular;
    the flaps of the pair of flaps are substantially rectangular, square, or trapezoidal; and
    the panel is substantially rectangular, square, or trapezoidal.

6. The external nasal dilation device of claim 5, wherein:
    corners of the pads of the pair of pads are arcuate or right angled;
    corners of the panel are arcuate or right angled; and
    corners of the flaps distal from the pads are arcuate or right angled.

7. The external nasal dilation device of claim 5, wherein opposed side edges of the panel are substantially parallel to opposing edges of the flaps of the pair of flaps.

8. The external nasal dilation device of claim 5, wherein opposed side edges of the panel are non-parallel to opposing edges of the flaps of the pair of flaps.

9. The external nasal dilation device of claim 1, wherein the panel is dimensionally narrower than the flaps of the pair of flaps.

10. The external nasal dilation device of claim 1, wherein at least one of the second connector and the respective first connector comprises a magnet.

11. The external nasal dilation device of claim 1, wherein the panel has a nontensioned configuration that is arcuate or substantially planar.

12. An external nasal dilation device comprising:
    a pair of pads, the pads of the pair of pads being substantially rectangular, square, oval, or circular, corners of the pads of the pair of pads being arcuate or right angled;
    adhesive positioned on a lower face of each pad of the pair of pads, wherein the adhesive is configured for removably attaching the pads of the pair of pads to opposed sides of a nose of a user;
    a pair of sheets, each sheet of the pair of sheets being removably attached to the adhesive positioned on a respective pad of the pair of pads, such that the adhesive is substantially covered by the sheet, the sheet being selectively detachable from the respective pad for exposing the adhesive, wherein the sheets are configured for preventing inadvertent adhesion of the adhesive;
    a pair of flaps, each flap of the pair of flaps being hingedly attached to an upper face of a respective pad of the pair of pads, such that each flap of the pair of flaps is hingable relative to the respective pad, each flap of the pair of flaps being attached to the respective pad substantially equally distant from opposed ends of the respective pad, the flaps of the pair of flaps being substantially rectangular, square, or trapezoidal, corners of the flaps distal from the pads being arcuate or right angled;
    an panel attached to and extending between the flaps of the pair of flaps, the panel being resiliently flexible, such that the panel is configured to extends arcuately over a bridge of the nose, wherein the panel is configured for exerting opposing forces to nostrils of the user for expanding the nostrils, the panel comprising one or more of elastomer, plastic, and spring metal, the panel being substantially rectangular, square, or trapezoidal, corners of the panel being arcuate or right angled, the panel being dimensionally narrower than the flaps of the pair of flaps, opposed side edges of the panel being substantially parallel to opposing edges of the flaps of the pair of flaps, the panel having a nontensioned configuration that is arcuate or substantially planar;
    a pair of first connectors, each first connector of the pair of first connectors being attached to a respective flap of the pair of flaps; and
    a pair of second connectors, each second connector of the pair of second connectors being attached to the panel proximate to a respective opposing end of the panel, the second connectors being complementary to the first connectors, such that each second connector of the pair of second connectors is positioned for selectively engaging a respective first connector of the pair of first connectors for removably attaching the panel to the pair of flaps.

13. The external nasal dilation device of claim 12, wherein at least one of the second connector and the respective first connector comprising a magnet.

14. A method of dilating nostrils of a user comprising the steps of:

providing an external nasal dilation device comprising:

a pair of pads, adhesive positioned on a lower face of each pad of the pair of pads, a pair of flaps, each flap of the pair of flaps being hingedly attached to an upper face of a respective pad of the pair of pads, such that each flap of the pair of flaps is hingable relative to the respective pad, a panel attached to and extending between the flaps of the pair of flaps, the panel being resiliently flexible;

a pair of first connectors, each first connector of the pair of first connectors being attached to a respective flap of the pair of flaps; and a pair of second connectors, each second connector of the pair of second connectors being attached to the panel proximate to a respective opposing end of the panel, the second connectors being complementary to the first connectors, such that each second connector of the pair of second connectors is positioned for selectively engaging a respective first connector of the pair of first connectors for removably attaching the panel to the pair of flaps;

removably attaching one pad of the pair of pads to one opposed side of a nose of the user using the adhesive;

flexing the panel to position the other pad of the pair of pads proximate to the other opposed side of the nose, such that the panel extends arcuately over a bridge of the nose;

removably attaching the other pad of the pair of pads to the other opposed side of the nose using the adhesive; and allowing the panel to exert opposing forces to the nostrils of the user for expanding the nostrils.

\* \* \* \* \*